(12) United States Patent
Richardson et al.

(10) Patent No.: US 11,226,309 B2
(45) Date of Patent: Jan. 18, 2022

(54) TECHNIQUES FOR PREDICTING COLLISION CROSS-SECTION VALUES

(71) Applicant: WATERS TECHNOLOGIES IRELAND LIMITED, Dublin (IE)

(72) Inventors: Keith G. Richardson, High Peak (GB); Hans Vissers, Huizen (NL)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 0 days.

(21) Appl. No.: 16/849,229

(22) Filed: Apr. 15, 2020

(65) Prior Publication Data
US 2020/0326303 A1    Oct. 15, 2020

Related U.S. Application Data

(60) Provisional application No. 62/834,084, filed on Apr. 15, 2019.

(51) Int. Cl.
*G01N 27/64* (2006.01)
*G01N 27/622* (2021.01)
*H01J 49/00* (2006.01)

(52) U.S. Cl.
CPC .......... *G01N 27/622* (2013.01); *G01N 27/64* (2013.01); *H01J 49/0031* (2013.01); *H01J 49/0036* (2013.01)

(58) Field of Classification Search
CPC ... G01N 27/622; G01N 27/64; H01J 49/0031; H01J 49/0036; H01J 49/004; G06N 3/02; G16C 20/70; G16C 20/20
USPC ................................................. 250/281, 282
See application file for complete search history.

(56) References Cited

U.S. PATENT DOCUMENTS

2018/0197726 A1\* 7/2018 Yamaguchi .......... G06K 9/4652

OTHER PUBLICATIONS

Zhou, et al ("Large-scale prediction of collision cross-section values for metabolites in ion mobility mass spectrometry" Analytical Chemistry, vol. 88, No. 22, pp. 11084-11091 (2016) (Year: 2016).\*
International Search Report and Written Opinion for International application No. PCT/IB2020/053569, dated Aug. 31, 2020, 14 pages.
Zhou, Z., et al., "Large-Scale Prediction of Collision Cross-Section Values for Metabolites in Ion Mobility-Mass Spectrometry", Analytical Chemistry 88(22):11084-11091 (2016).

(Continued)

*Primary Examiner* — Michael Maskell
(74) *Attorney, Agent, or Firm* — Kacvinsky Daisak Bluni PLLC

(57) ABSTRACT

Techniques and apparatus for generated predicted collision cross-section (CCS) values based on a hybrid CCS prediction processes are described. In one embodiment, for example, an apparatus may include at least one memory, and logic coupled to the at least one memory. The logic may be configured to implement a predicted CCS process, for example, by receiving analytical information from analysis of a sample using an ion mobility spectrometry instrument, the sample comprising at least one component, generating an approximate molecular model for the component via an approximate molecular modeling process, and generating a predicted CCS value via a computational model based on the approximate molecular model. Other embodiments are described.

20 Claims, 8 Drawing Sheets

(56) References Cited

OTHER PUBLICATIONS

Plante, P-L., et al., "Predicting Ion Mobility Collision Cross-Sections Using a Deep Neural Network: DeepCCS", Analytical Chemistry 91(8):5191-5199 (2019).
Zhou, Z., et al., "MetCCS Predictor: A Web Server for Predicting Collision Cross-Section Values of Metabolite in Metabolomics", Bioinformatics 33:2235-2237 (2017).
Zhou, Z., et al., "Advancing the large-scale CCS database for metabolomics and lipidomics at the machine-learning era", Current Opinion in Chemical Biology 42:34-41 (2017).

* cited by examiner

TECHNIQUES FOR PREDICTING COLLISION CROSS-SECTION VALUES

CROSS-REFERENCE TO RELATED APPLICATIONS

This application claims the benefit of and priority to U.S. Provisional Patent Application No. 62/834,084, filed on Apr. 15, 2019, the entire contents of which is hereby incorporated by reference.

TECHNICAL FIELD

Embodiments herein generally relate to processing analytical data and, more specifically, to predicting collision cross-section values based on analytical information derived from ion mobility analysis of a sample.

BACKGROUND

Ion mobility spectrometry or separation (IMS) is a widely used technique for identifying and quantifying compounds within a sample. In general, IMS operates by separating gas-phase ions based on their shape, size, and charge by subjecting the ions to a weak electric field in the presence of an inert buffer gas, such as nitrogen or helium. Ions of different sizes and shapes will have different collision frequencies with the inert buffer gas as the ions flow through a separation or mobility cell of an IMS device. Collisions between the ions and the inert buffer gas under the influence of the electric field produce differences in drift time of ions (i.e., ions with a higher collision frequency will have a higher drift time compared with ions with a lower collision frequency). Properties associated with IMS include the drift time, ion mobility, collision cross-section (CCS) or ($\Omega$), and/or reduced CCS ($\Omega'$). Ions separated by IMS may be introduced into a mass analyzer (e.g., a mass spectrometer (MS)) to determine further physiochemical properties, such as mass-to-charge (m/z) ratios.

The use of CCS for identification and confirmation of compound identity in sample experiments may provide orthogonal compound characteristics, under given experimental conditions, to retention time and tandem MS information. However, conventional approaches are deficient for widespread use due to, among other things, a lack of CCS measurements in compound libraries and the availability of computational tools to rapidly generate theoretical CCS values. Accordingly, analysts using CCS to evaluate sample components may benefit from methods of obtaining CCS values that are more efficient and effective than conventional systems.

DETAILED DESCRIPTION

Figure 1:
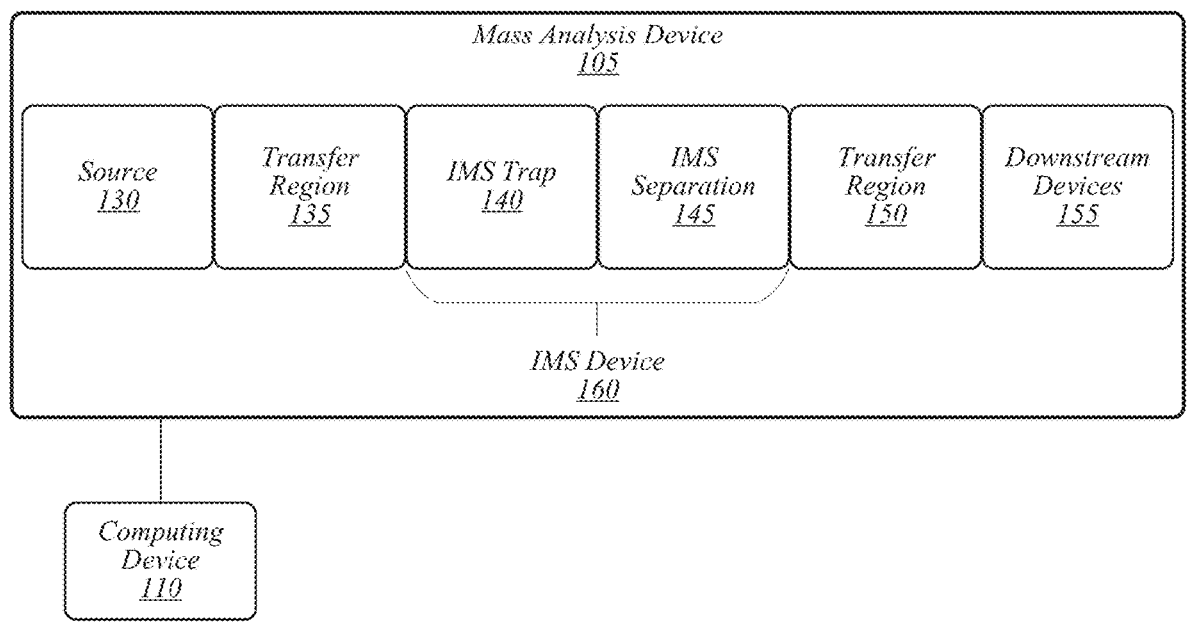
FIG. 1 illustrates an embodiment of a first operating environment.

Various embodiments may generally be directed toward systems, methods, and/or apparatus for predicting collision cross-section (CCS) or ($\Omega$). In some embodiments, predicted CCS or reduced CCS values (pCCS) may be determined using a CCS prediction (hybrid modeling or hybrid CCS prediction) process that combines molecular modeling techniques with machine learning techniques, including, without limitation, artificial intelligence processes, neural networks, and/or the like. In various embodiments, the CCS prediction process may include generating one or more pCCS values for various forms of a compound, such as different charge states, conformers, isomers, isobars, and/or the like.

In some embodiments, analytical information associated with a sample or a portion thereof may be obtained. In various embodiments, the sample may include a plurality of components or a single component, such as a single molecule of interest. The analytical information may include various properties, characteristics, descriptors, elements, and/or the like of a component. For example, the properties may include a description of a molecule (for instance, a 2D or connectedness description) alone or in combination with known and/or theoretical physicochemical properties of the molecule.

In some embodiments, the properties may be theoretical, determined via analytical analysis, or a combination thereof. For example, in exemplary embodiments, analytical information may include data obtained via mass analysis (i.e., IMS, MS, IM-MS, CCS analyses (i.e., derived from drift time), and/or the like) of a sample that may be used to form an approximate molecular model of a compound of interest. In various embodiments, the approximate molecular model may be or may include pseudo 3D molecular descriptors, for instance, that may be provided to a machine learning process to generate pCCS values. In some embodiments, the approximate molecular model may include 2D descriptions, connectedness descriptions, and/or the like of a molecule. The approximate molecular model may be generated by performing an approximate, rough, abbreviated, and/or the like molecular modeling process to determine a set of conformations of the molecule in substantially reduced time (e.g., on a scale of seconds to minutes) than required to form a full model using conventional techniques (on the scale of hours to days). For example, the approximate molecular modeling process may only perform a limited number of modeling cycles, may only determine a limited number of properties, may determine relative values, descriptors, factors, or other distinguishing elements, and/or the like. In some embodiments, the approximate molecular model may include possible energy states, ionization states or vibrational states of the molecule. The approximate molecular model may be provided to a CCS computational model (e.g., machine learning process, neural network, artificial intelligence processes, and/or the like) operative to generate pCCS values based on (2D) molecular descriptors and properties (including approximate molecular models generated according to some embodiments) to complement measured data in order to build a prediction model.

IMS and/or IM-MS may be applied in various fields, including, without limitation, drug development (i.e., drug metabolism and pharmacokinetics (DMPK)), food and environment (F&E) studies, toxicology, metabolomics and other "omics" studies, and/or the like. For example, the use of CCS (for example, rotationally averaged CCS) for identification and confirmation of compound identity may provide an orthogonal physicochemical supplement to retention time and MS information. At least one limiting factor in conventional systems is a lack of CCS measurements in compound libraries and the availability of computational tools to rapidly generate theoretical CCS values, either calculated using molecular modeling approaches or predicted with machine learning (i.e., neural networks, artificial intelligence processes, and/or the like) based tools, from structure. Accordingly, some embodiments provide a hybrid model that incorporates molecular modeling principles into a machine learning based approach, which can take advantage of the strengths of both methods.

In some embodiments, the approximate molecular models may be used to "train" a CCS calculation or determination algorithm, process, model, and/or the like. In various embodiments, training a CCS calculation algorithm may include experimental information. In exemplary embodiments, training a CCS calculation algorithm not require actual experimental information or may use a combination of experimental and non-experimental (for instance, library or theoretical information) information. For example, the CCS values may be derived from a library of known or previously determined CCS values, from a sophisticated ab initio molecular modelling and CCS calculation workflow, and/or the like.

In various embodiments, a CCS prediction process may include using approximate molecular models (alone or in combination with other known physicochemical information) for a set of first components having known CCS values to configure a CCS calculation algorithm, and using the CCS calculation algorithm to calculate CCS values for one or more second components, which may not have known CCS values. In general, there may not be a need to measure the CCS values for the second components experimentally. The calculated CCS values for the second components may be used to optimize or plan possible future experiments.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, a mass analysis device 105 (for instance, an IM-MS device) may include an ion source 130, with a first ion transfer region 135 arranged downstream of ion source 130. An IMS device 160 may be arranged downstream of ion source 130 and first transfer region 135. IMS device 160 may include an IMS trap region 140 and an IMS separation region 145. An optional second transfer region 150 may be arranged downstream of IMS device 160.

In some embodiments, one or more downstream devices or stages 155 may optionally be arranged downstream of second transfer region 150. Downstream devices 155 may include various devices such as, without limitation, a mass analyzer, a mass filter, and/or one or more other analytical devices. For example, downstream devices 155 may include a Time of Flight ("ToF") mass analyzer, one or more quadrupole mass filters, one or more ion traps, and/or the like. According, in some embodiments, IMS device 160 may be coupled between ion source 130 and the one or more downstream devices 155. Embodiments are not limited in this context.

Figure 2:
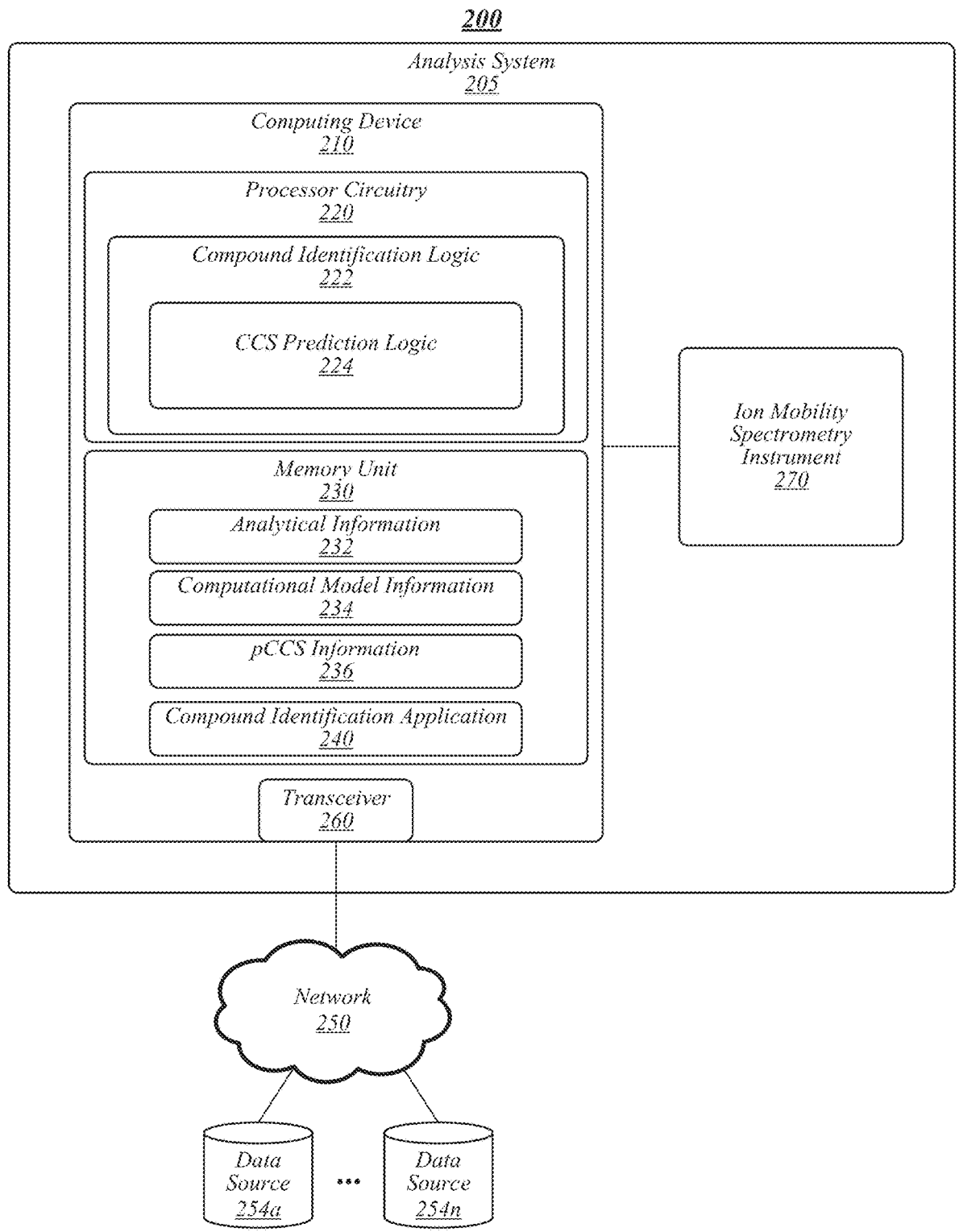
FIG. 2 illustrates an embodiment of a second operating environment.
Figure 7:
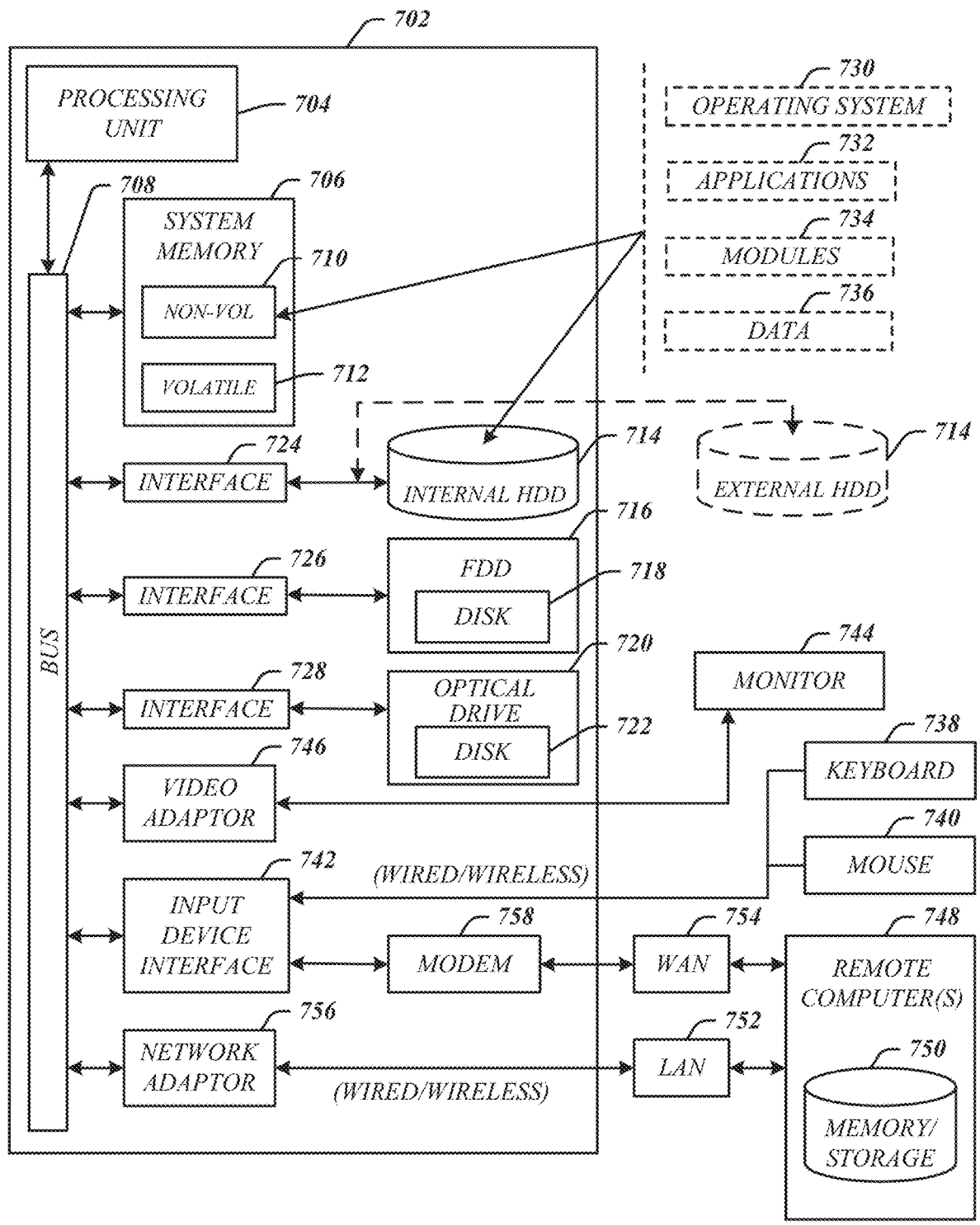
FIG. 7 illustrates an embodiment of a computing architecture.

In various embodiments, mass analysis device 105 and/or portions thereof, may be operably coupled to a computing device 110 (see, for example, FIGS. 2 and 7). In some embodiments, computing device 110 may operate to control various functions of mass analysis device and/or data processing functions associated with analytical information obtained from mass analysis device 105. For example, computing device 110 may operate to determine various physicochemical properties of sample components analyzed via mass analysis device.

FIG. 2 illustrates an example of an operating environment 200 that may be representative of some embodiments. As shown in FIG. 2, operating environment 200 may include an analysis system 205 operative to manage analytical information 232, for example, associated with ion mobility spectrometry instrument 270. In some embodiments, ion mobility spectrometry instrument 270 may be or may include an IMS device, an IM-MS device, and/or the like (see, for example, FIG. 1). In various embodiments, ion mobility spectrometry instrument 270 may include certain other components, including, without limitation, a chromatography system, a liquid chromatography (LC) system, a gas chromatography (GC) system, a mass analyzer system, a mass detector system, a high-performance liquid chromatography (HPLC) system, a ultra-performance liquid chromatography (UPLC®) system, a ultra-high performance liquid chromatography (UHPLC) system, an ultraviolet (UV) detector, a visible light detector, a solid-phase extraction system, a sample preparation system, a sample introduction system, a pump system, a capillary electrophoresis instrument, combinations thereof, components thereof, variations thereof, and/or the like.

In some embodiments, ion mobility spectrometry instrument 270 may operate to perform an analysis and generate analytical information 232. In various embodiments, analytical information 232 may include information, data, files, charts, graphs, images, spectra, peak lists, mass values, retention time values, concentration values, compound identification information, and/or the like generated by an analytical instrument as a result of performing an analysis method. For example, ion mobility spectrometry instrument 270 may generate analytical information 232 in the form of mass-to-charge (m/z) information, drift time ($t_d$) information, ion mobility information, CCS information, and/or the like.

In various embodiments, analytical information 232 may include non-experimental information, including, without limitation, theoretical information, library information of known data, and/or the like. The analytical information may include various properties, characteristics, descriptors, elements, and/or the like of a component. For example, the properties may include a description of a molecule (for instance, a 2D or connectedness description) alone or in combination with known and/or theoretical physicochemical properties of the molecule. In some embodiments, the properties may be theoretical, determined via analytical analysis, or a combination thereof In various embodiments, analysis system 205 may include computing device 210 communicatively coupled to ion mobility spectrometry instrument 270 or otherwise configured to receive and store analytical information 232 associated with analytical device 215. In some embodiments, computing device 210 may receive at least a portion of analytical information 232 from ion mobility spectrometry instrument 270. In various embodiments, computing device 210 may receive at least a portion of analytical information 232 from data sources 254a-n via network 250. For example, ion mobility spectrometry instrument 270 may operate to provide analytical information 232 directly to computing device 210 and/or to a location on a network 250 (for instance, a cloud computing environment) accessible to computing device 210.

In some embodiments, computing device 210 may be operative to control, monitor, manage, or otherwise process various operational functions of ion mobility spectrometry instrument 270. In some embodiments, computing device 210 may be operative to provide analytical information 232 to a location on a network 250 through a secure or authenticated connection. In some embodiments, computing device 210 may be or may include a stand-alone computing device, such as a personal computer (PC), server, tablet computing device, cloud computing device, mobile computing device (for instance, a smart phone, tablet computing device, and/or the like), data appliance, and/or the like. In various embodiments, computing device 210 may be or may include a controller or control system integrated into ion mobility spectrometry instrument 270 to control operational aspects thereof.

Although only one computing device 210 is depicted in FIG. 2, embodiments are not so limited. In various embodiments, the functions, operations, configurations, data storage functions, applications, logic, and/or the like described with respect to computing device 210 may be performed by and/or stored in one or more other computing devices. A single computing device 210 is depicted for illustrative purposes only to simplify the figure.

As shown in FIG. 2, computing device 210 may include processor circuitry 220, a memory unit 230, and a transceiver 260. Processor circuitry 220 may be communicatively coupled to memory unit 230 and/or transceiver 260.

Processor circuitry 220 may include and/or may access various logics for performing processes according to some embodiments. For instance, processor circuitry 220 may include and/or may access compound identification logic 222 and/or CCS prediction logic 224. Processing circuitry 220 and/or compound identification logic 222 and/or CCS prediction logic 224, and/or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 400. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although compound identification logic 222 is depicted in FIG. 2 as being within processor circuitry 220, embodiments are not so limited. In addition, although CCS prediction logic 224 is depicted as being a logic of processor circuitry 220, embodiments are not so limited, as data processing logic 224 may be a standalone logic. For example, compound identification logic 222, and/or any component thereof, may be located within an accelerator, a processor core, an interface, an individual processor die, implemented entirely as a software application (for instance, compound identification application 240) and/or the like.

Memory unit 230 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 230 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 230 may store a compound identification application 240 that may operate, alone or in combination with compound identification logic 222, to perform various analytical services according to some embodiments. For example, compound identification application 240 may operate to identify compounds in a sample. In another example, compound identification application 240 may operate to perform a hybrid CCS prediction processes to generate pCCS values according to some embodiments, for instance, via CCS prediction logic 224. In exemplary embodiments, compound identification application 240 may generate pCCS values as part of a process for identifying compounds in a sample. In various embodiments, identifying compounds may include identifying "known knowns" (i.e., known compounds anticipated as being a part of the sample), "known unknowns" (i.e., known compounds not anticipated as being a part of the sample), and/or "unknown unknowns" (i.e., unknown compounds within the sample).

Figure 3:
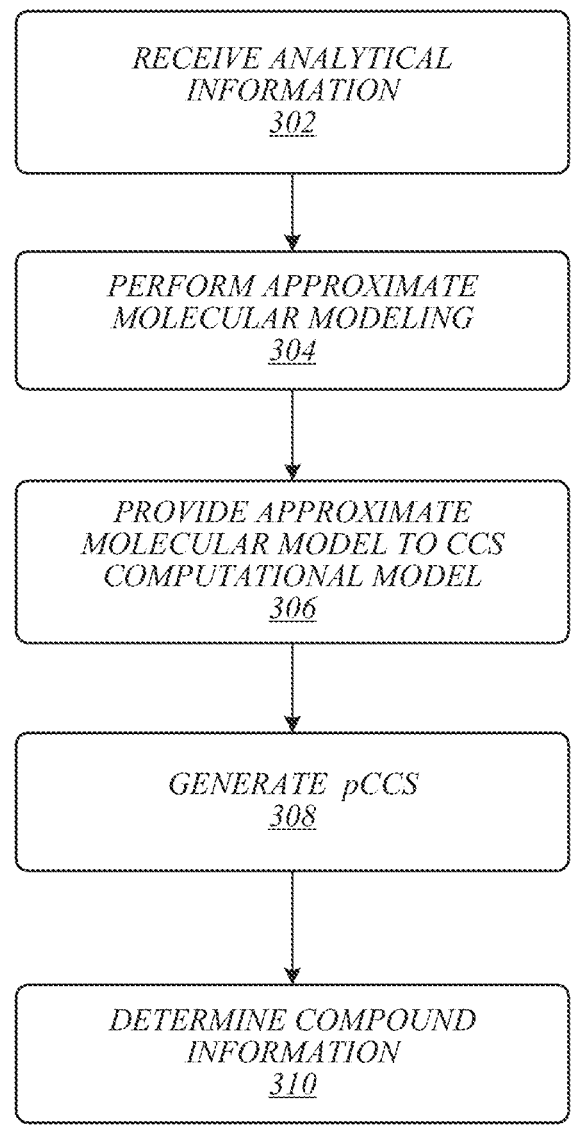
FIG. 3 illustrates an embodiment of a first logic flow.

In various embodiments, compound identification application 240 may use computational model information 234 to identify compounds and/or generate pCCS information (see, for example, FIG. 3). In some embodiments, computational model information 234 may include molecular modeling information, process, and/or the like operative to model a molecule based on analytical information. Non-limiting examples of modeling processes may include a structural calculation step followed by a CCS calculation step for one or more of the structures thus identified. The structural calculation step may include generating initial 3D structures from 2D coordinates, identifying a set of one or more possible conformers (for instance, about five conformers) from these initial 3D structures, obtaining an optimized structure for each conformer. The step of calculating a CCS value from a structure may include one or more of the trajectory method, the exact hard sphere scattering method, the projection approximation, scattering from electron density isosurfaces (SEDI), the projection superposition approximation (PSA) and many other methods of CCS calculation. The step of generating an optimized structure may include energy minimization. Examples of software that may be used to calculate structures and carry out energy minimization may include Avogadro, Gaussian, GAMESS, and/or the like. Examples of software that may be used to calculate CCS values given structures include MobCal, IMOS, CCScalc, and/or the like. Embodiments are not limited to these example modeling processes, as any molecular modeling process capable of operating according to some embodiments is contemplated herein.

In various embodiments, molecular modeling processes may be configured to model at least a portion of a molecule or other compound being analyzed. In some embodiments, a molecular model may include various factors, elements, descriptors (e.g., pseudo or relative 3D geometry), and/or the like associated with a molecule. Non-limiting examples of descriptors may include charge, size, shape, and/or the like. In various embodiments, the descriptors may include all or substantially all of the descriptors associated with a particular molecular modeling process. In exemplary embodiments, the descriptors may include a subset of the descriptors associated with a particular modeling process. In some embodiments, the subset of descriptors may be selected based on their contribution to the determination of CCS (or pCCS).

In exemplary embodiments, computational model information 234 may include various machine learning processes, algorithms, and/or the like. In some embodiments, the machine learning processes may be trained using training data, such as actual CCS values experimentally determined for known molecules. Non-limiting examples of machine learning processes may include MetCCS (see, for example, Zhou et al., "MetCCS Predictor: A Web Server for Predicting Collision Cross-Section Values of Metabolite in Metabolomics", Bioinformatics, 2017, 33, 2235-2237), DeepCCS (see, for example, Plante et al., "Predicting Ion Mobility Collision Cross-Sections Using a Deep Neural Network: DeepCCS," Analytical Chemistry (April 2019)). In some embodiments, machine learning processes may be or may include cross-validation (CV) processes. Embodiments are not limited to these example machine learning processes, as any machine learning process capable of operating according to some embodiments is contemplated herein.

In some embodiments, compound identification application 240 may generate analytical information 232 in the form of experimental information. In various embodiments, experimental information may include compound information for known compounds, such as drift time, CCS, m/z, and/or the like. Experimental information of known compounds may be used as part of a modeling process and/or machine learning process according to some embodiments to determine certain characteristics of unknown compounds. For example, experimental CCS data may be obtained from calibrated travelling wave based IMS measurements acquired with IMS-Q-oaToF and Q-IMS-oaToF configurations. In general, the experimental data may represent the average of the measurement of at least three technical replicates. In total, here, 4,100 CCS values from close to 3,000 different compounds, representing various adducted forms of the compounds and ten chemical classes, may be used for training, validation, and/or testing of models according to some embodiments.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. Embodiments are not limited in this context.

FIG. 3 illustrates an embodiment of a logic flow 300. Logic flow 300 may be representative of some or all of the operations executed by one or more embodiments described herein, such as by computing devices 110 and/or 210. For instance, logic flow 300 may be representative of some or all of the operations of generating pCCS values according to some embodiments.

At block 302, logic flow 300 may receive analytical data. For example, analytical information 232 resulting from analyzing a sample via ion mobility spectrometry instrument 270 may be accessed by compound identification application 240.

Logic flow 300 may perform approximate molecular modeling at block 304. For example, at least a portion of analytical information (for instance, drift time, m/z, ion mobility, and/or the like) may be provided to a molecular modeling process to perform an approximate molecular modeling process. Full molecular modeling processes using known techniques require a large amount of computing resources and time (for instance, in the range of hours to days) to generate a molecular model. Accordingly, some embodiments may perform an approximate molecular modeling process in which only a subset of descriptors, cycles, and/or the like are determined or performed. For example, a conventional molecular modeling process may require X cycles or optimization energy steps; however, some embodiments may only perform N cycles, where N<X (or even N<<X). For example, X may be greater than 100 and N may be less than 100. In some embodiments, N may be 1, 2, 3, 4, 5, 10, 15, 20, 50, 100, 200, 250, 500, 1000, 5000, and/or any value or range between any two of these values (including endpoints). An approximate molecular modeling process may generate an approximate molecular model, representing a rough model of a molecule. In various embodiments, an approximate molecular model may include possible forms of the molecule, including charge states, conformer states, and/or the like. The approximate molecular model may be generated in less time than a full model, for instance, in the range of seconds or minutes. For instance, an approximate molecular model may be generated in about 100 milliseconds (ms), about 1 second (s), about 5 s, about 10 s, about 30 s, about 1 minute (m), about 5 m, about 10 m, about 30 m, and/or any value or range between any two of these values (including endpoints).

In some embodiments, the structure (or approximate or relative structure) may be determined based on the analytical information. The number of possible conformers that can be generated may depend, at least partially, on the structure of the compound. In addition, in some embodiments, the structure may determine how long it takes to optimize the energy/conformation (for example, 10 s for a small rigid molecule, up to 5-6 min for a more flexible/larger molecule, and/or the like) per conformer.

In some embodiments, the approximate molecular modeling process may generate a plurality of molecular models, for example, each with for a different charge state or configuration. For example, the CCS of an ion may be related to the shape, size, and/or charge state of the ion. Ions for the same molecule may have different charge states. Accordingly, multiple approximate molecular models may be generated for a molecule, for instance, a plurality of models with different models for different charge states. In some embodiments, the approximate molecular model may be or may provide (pseudo) molecular descriptors associated with a sample component. In various embodiments, these pseudo molecular descriptors may be used by a machine learning process according to some embodiments to generate a pCCS value.

Logic flow 300 may provide the approximate molecular model to a CCS computational model at block 306. For example, computational model information 234 may include various machine learning processes operative to determine a pCCS based a molecular model. Compound identification application 240 may provide the approximate molecular model to a machine learning process of computational model information 234. At block 308, pCCS may be generated by logic flow. For example, the machine learning process may generate pCCS information 236 including at least one pCCS value. In various embodiments, a plurality of pCCS values may be generated for one molecule, one approximate molecular model, and/or the like. For example, a plurality of pCCS values may be generated for different conformations, charge states, and/or the like of a molecule. In some embodiments, a rough model may be used to predict CCS more efficiently and with improved accuracy over conventional processes. In various embodiments, a CCS prediction process (for instance, via a machine learning or artificial intelligence process) may operate to generate a pCCS value based on pseudo molecular descriptors of an approximate molecular model generated according to some embodiments.

At block 310, logic flow 310 may determine compound information. For example, compound identification application 240 may use pCCS information 236 to determine or estimate the identify of a molecule of interest based on a pCCS value.

Example

Hybrid CCS Prediction Processes

A hybrid CCS prediction process was performed according to some embodiments. Experimental CCS data were obtained from travelling wave based IMS measurements acquired with IMS-Q-oaToF and Q-IMS-oaToF geometries. In general, the experimental data may represent the average of the measurement of at least three technical replicates. In total, 4,100 CCS values from close to 3,000 different compounds, representing various adducted forms of the compounds and ten chemical classes, were used for model training, validation and testing. For molecular modeling, Avogadro (oBabel) and CCScalc (included within DriftScope) were applied to provide structural/geometrical information, in the form of various constants, and projection approximation calculations, respectively, and a gradient boosting algorithm to train a predictive model with features including relevant molecular descriptors and structural features obtained using a molecular modeling approach, for instance, via an approximate molecular modeling process.

A hybrid CCS prediction model was developed on and evaluated with experimental CCS data of singly charged compounds using a Cross-Validation (CV) strategy, external data, and multiple use-cases. The CV results showed a significant improvement over a baseline model that is solely based on molecular weight, with the relative mean absolute error of the baseline model improved from 4.6%, compared to 1.8% in anon-hybrid (machine learning only) model, and observed for all molecular and chemical classes, even for the more complex chemical super classes such as benzenoids and organoheterocyclic compounds, which are harder to predict.

The process results were also compared to difference conventional machine learning approaches and showed overall improved performance. In some embodiments, training several models is not required; for example, a single model according to some embodiments produced high quality results as long as a sufficiently diverse training data set is employed.

In the final evaluation, the predictive model was applied to the problem of CCS prediction for positional isomers and isobaric molecules according to some embodiments. In the majority of these cases, the model was able to predict the rank order of analyte CCS values correctly, demonstrating that predicted CCS values can augment down-stream analysis. To further demonstrate the impact on down-stream analysis, an evaluation metric was used that reflects the model's discrimination capability for isobaric analytes. This metric apportions the measured CCS library data into isobaric bins and for each compound within the bin, the closest observed and predicted CCS values are assigned and compared to the CCS value of the actual compound. In the majority of the cases, the closest predicted and observed CCS pair was found to be the actual compound of interest, which suggests that incorporation of predicted CCS values can improve discrimination of isobaric compounds.

Figure 4:
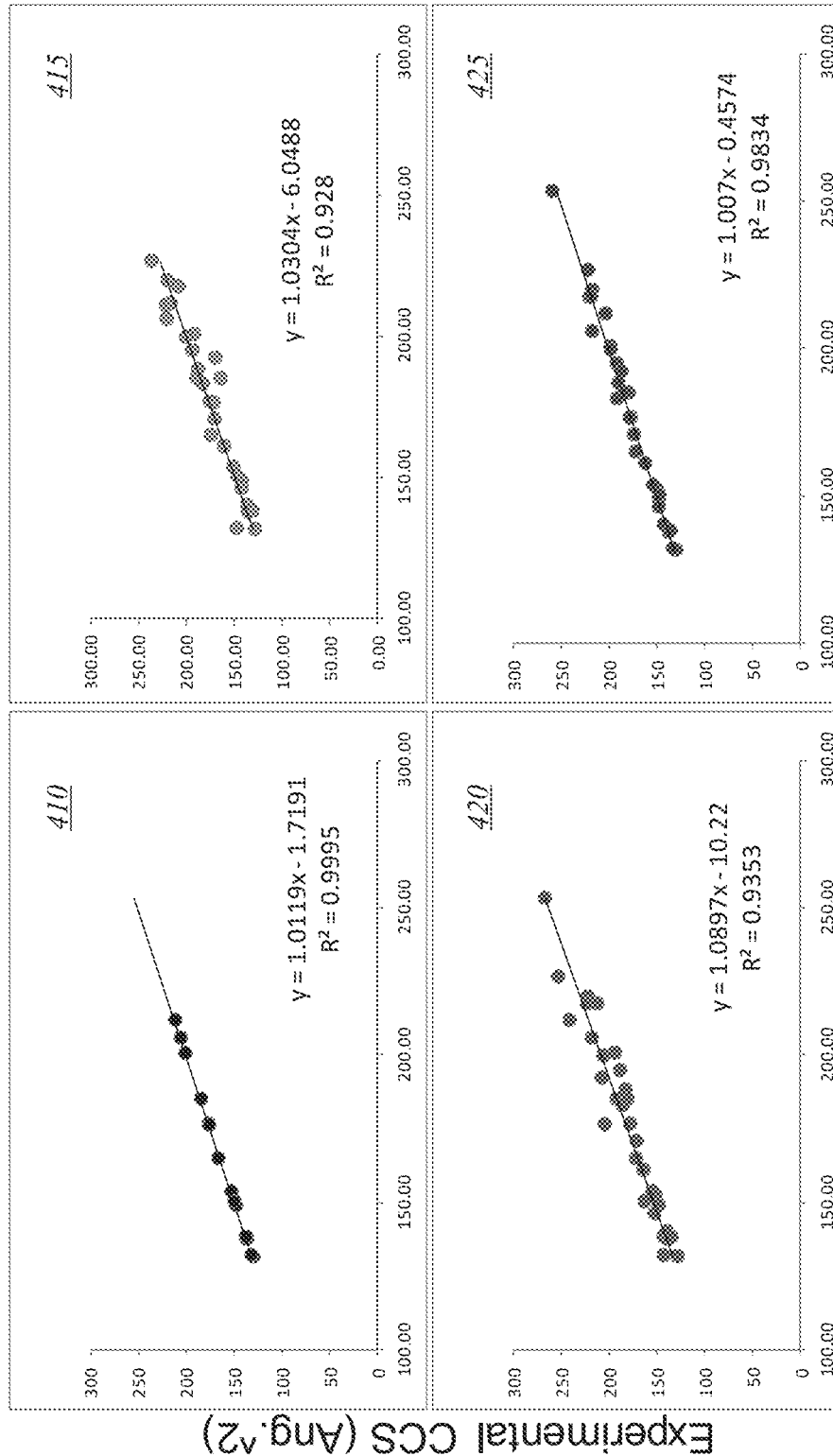
FIG. 4 illustrates experimental collision cross-section (CCS) vs. predicted CCS for various processes.
Figure 5:
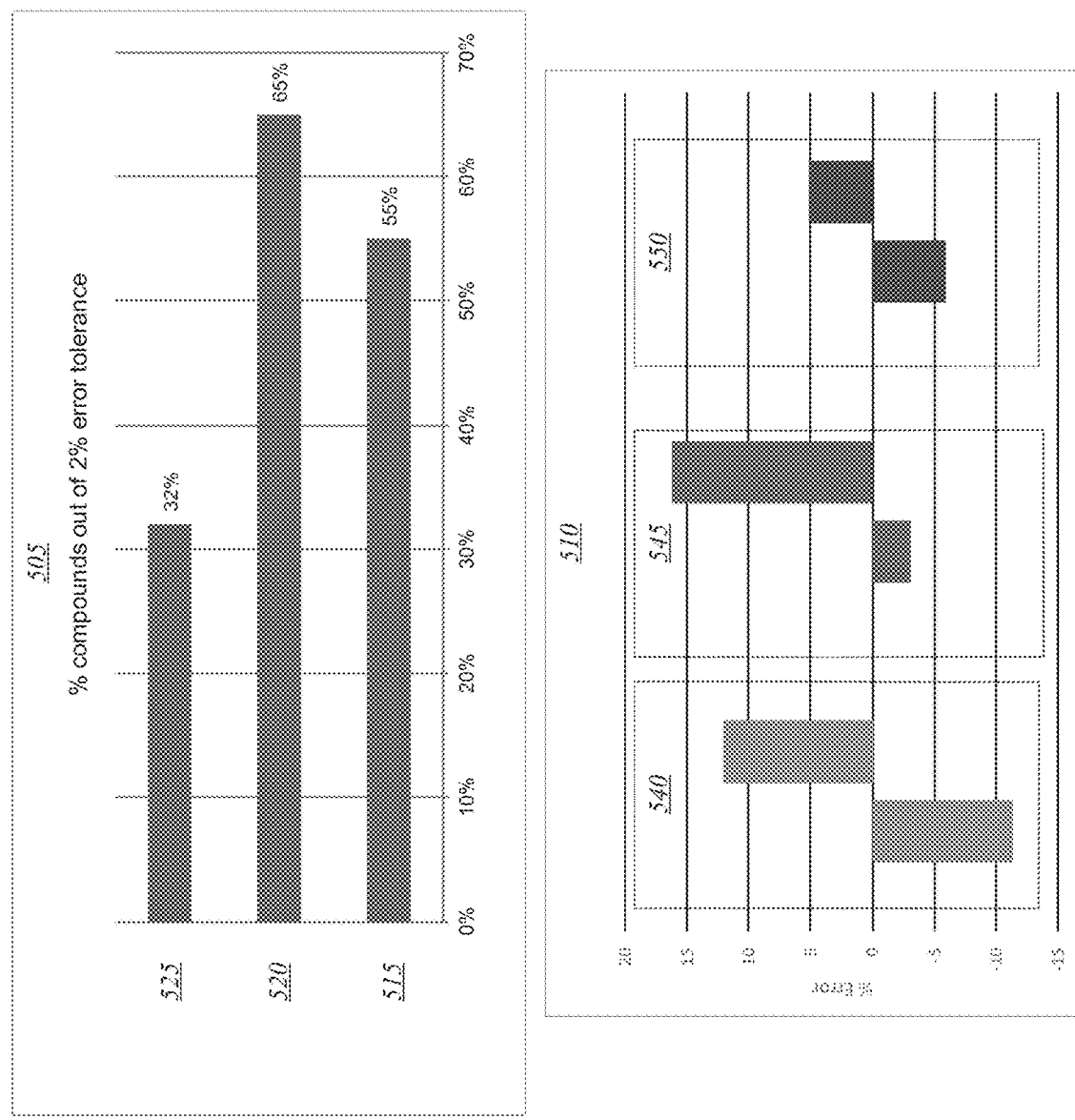
FIG. 5 illustrates error percentages for various CCS prediction processes.

FIGS. 4 and 5 depict comparisons of predicted CCS results for certain conventional processes compared with the hybrid CCS prediction process according to some embodiments. FIG. 4 depicts experimental CCS vs. predicted CCS for various processes. In particular, graph 410 depicts standard CCS values, graph 415 depicts a first conventional CCS prediction process, graph 420 depicts a second conventional CCS prediction process, and graph 425 depicts a hybrid CCS prediction process according to some embodiments. The first conventional CCS prediction process may include a process as described in Bijlsma, Lubertus et al. "Prediction of Collision Cross-Section Values for Small Molecules: Application to Pesticide Residue Analysis." *Analytical chemistry* 89 12 (2017): 6583-6589 ("Bijlsma"). The second conventional CCS process may include MetCCS.

FIG. 5 depicts graph 505 showing the percentage of compounds out of 2% error tolerance for CCS prediction for a hybrid CCS prediction process according to some embodiments 525, Bijlsma 520, and MetCCS. Graph 510 depicts information for percent error CCS experimental vs. Bijlsma 540, percent error CCS experimental vs. MetCCS 545, and percent error CCS experimental vs. a hybrid CCS prediction process according to some embodiments 550.

As depicted in FIGS. 4 and 5, the hybrid CCS prediction process generated more accurate predictions than conventional processes, including Bijlsma and MetCCS.

Figure 6:
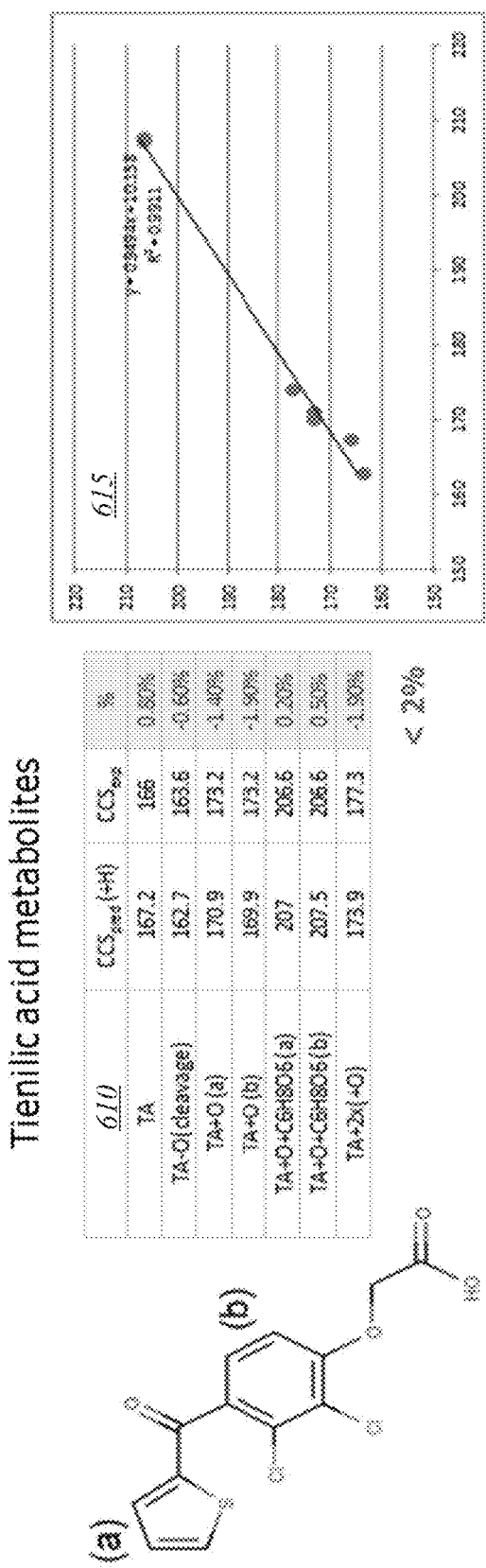
FIG. 6 illustrates CCS prediction results for a CCS prediction process according to some embodiments.

FIG. 6 depicts CCS prediction results for tienlilic acid metabolites using a hybrid CCS prediction process according to some embodiments. As shown in FIG. 6, the percent difference for pCCS and experimental CCS (eCCS) is less than about 2%.

The results generated for FIGS. 4-6 were determined using the machine learning process without approximate modeling processes according to some embodiments.

Figure 8:
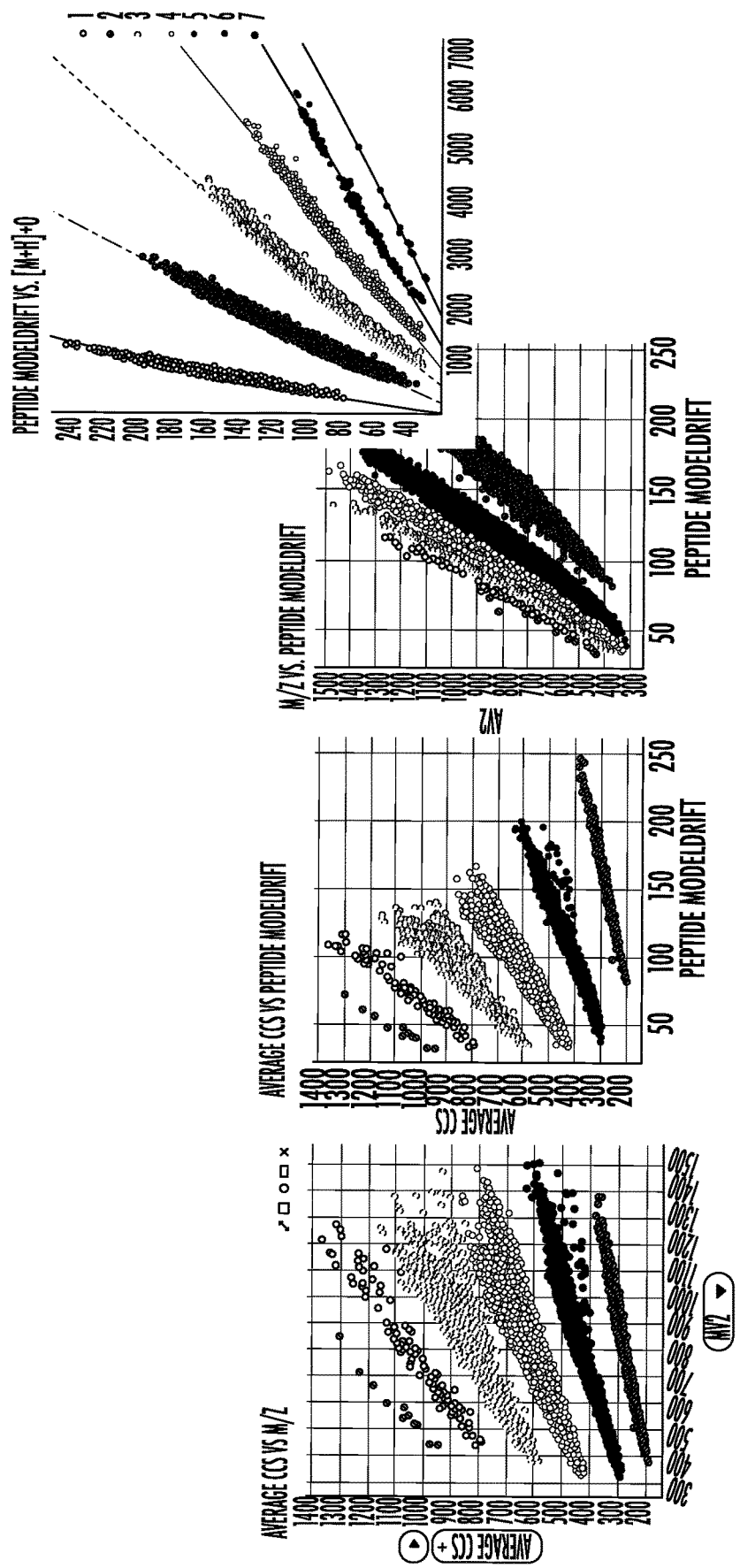
FIG. 8 depicts several graphs showing how model drift time correlates to empirical CCS (and other parameters), according to one case study.

FIG. 8 depicts another example in which the 'van der Waals' radius is used to derive 3D properties. These 3D properties can, in turn, be used by AI-based algorithms to predict CCS values. In one example, a model drift time may be calculated based on the following logic:

```
Modeldrift = -40.0 + 2.0 * CrossSectionalArea/z
// The collision cross section area (omega) is a function of
// the total Van der Waals volume, given by the formula:
// W=pi * (3/(4*pi))^(2/3)*V(2/3) = 1.209 * V^(2/3)
omega = 1.209 * Math.Pow(Volume, (2.0/3.0));
// "Volume" represents a sum of the "residueVolume" of each
// amino acid, which is the Van der Waals volume in
// cubic angstroms
```

FIG. 8 depicts how the model drift time (peptide.ModelDrift) correlates with empirical CCS and other parameters.

FIG. 7 illustrates an embodiment of an exemplary computing architecture 700 that may be suitable for implementing various embodiments as previously described. In various embodiments, the computing architecture 700 may comprise or be implemented as part of an electronic device. In some embodiments, the computing architecture 700 may be representative, for example, of a distributed processing system that implements or utilizes one or more components described herein. In some embodiments, computing architecture 700 may be representative, for example, of a compute node in a distributed processing system described herein that implements or utilizes one or more techniques described herein. The embodiments are not limited in this context.

As used in this application, the terms "system" and "component" and "module" may be intended to refer to a computer-related entity, either hardware, a combination of hardware and software, software, or software in execution, examples of which may be provided by the exemplary computing architecture 700. For example, a component may be, but may be not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server may be a component. One or more components may reside within a process and/or thread of execution, and a component may be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information may be implemented as signals allocated to various signal lines. In such allocations, each message may be a signal. Further embodiments, however, may alternatively employ data messages. Such data messages may be sent across various connections. Exemplary connections include parallel interfaces, serial interfaces, and bus interfaces.

The computing architecture 700 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, may be not limited to implementation by the computing architecture 700.

As shown in FIG. 7, the computing architecture 700 comprises a processing unit 704, a system memory 706 and a system bus 708. The processing unit 704 may be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 704.

The system bus 708 provides an interface for system components including, but not limited to, the system memory 706 to the processing unit 704. The system bus 708 may be any of several types of bus structure that may further interconnect to a memory bus (with or without a memory controller), a peripheral bus, and a local bus using any of a variety of commercially available bus architectures. Interface adapters may connect to the system bus 708 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 706 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 7, the system memory 706 may include non-volatile memory 710 and/or volatile memory 712. In some embodiments, system memory 706 may include main memory. A basic input/output system (BIOS) may be stored in the non-volatile memory 710.

The computer 702 may include various types of computer-readable storage media in the form of one or more lower speed memory units, including an internal (or external) hard disk drive (HDD) 714, a magnetic floppy disk drive (FDD) 716 to read from or write to a removable magnetic disk 718, and an optical disk drive 720 to read from or write to a removable optical disk 722 (e.g., a CD-ROM or DVD). The HDD 714, FDD 716 and optical disk drive 720 may be connected to the system bus 708 by a HDD interface 724, an FDD interface 726 and an optical drive interface 728, respectively. The HDD interface 724 for external drive implementations may include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules may be stored in the drives and memory units 710, 712, including an operating system 730, one or more application programs 732, other program modules 734, and program data 736. In one embodiment, the one or more application programs 732, other program modules 734, and program data 736 may include, for example, the various applications and/or components of message controller 104.

A user may enter commands and information into the computer 702 through one or more wire/wireless input devices, for example, a keyboard 738 and a pointing device, such as a mouse 740. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices may be often connected to the processing unit 704 through an input device interface 742 that may be coupled to the system bus 708, but may be connected by other interfaces such as a parallel port, IEEE 994 serial port, a game port, a USB port, an IR interface, and so forth.

A monitor 744 or other type of display device may be also connected to the system bus 708 via an interface, such as a video adaptor 746. The monitor 744 may be internal or external to the computer 702. In addition to the monitor 744, a computer typically includes other peripheral output devices, such as speakers, printers, and so forth.

The computer 702 may operate in a networked environment using logical connections via wire and/or wireless communications to one or more remote computers, such as a remote computer 748. In various embodiments, one or more migrations may occur via the networked environment. The remote computer 748 may be a workstation, a server computer, a router, a personal computer, portable computer, microprocessor-based entertainment appliance, a peer device or other common network node, and typically includes many or all of the elements described relative to the computer 702, although, for purposes of brevity, only a memory/storage device 750 may be illustrated. The logical connections depicted include wire/wireless connectivity to a local area network (LAN) 752 and/or larger networks, for example, a wide area network (WAN) 754. Such LAN and WAN networking environments may be commonplace in offices and companies, and facilitate enterprise-wide computer networks, such as intranets, all of which may connect to a global communications network, for example, the Internet.

When used in a LAN networking environment, the computer 702 may be connected to the LAN 752 through a wire and/or wireless communication network interface or adaptor 756. The adaptor 756 may facilitate wire and/or wireless communications to the LAN 752, which may also include a wireless access point disposed thereon for communicating with the wireless functionality of the adaptor 756.

When used in a WAN networking environment, the computer 702 may include a modem 758, or may be connected to a communications server on the WAN 754, or has other means for establishing communications over the WAN 754, such as by way of the Internet. The modem 758, which may be internal or external and a wire and/or wireless device, connects to the system bus 708 via the input device interface 742. In a networked environment, program modules depicted relative to the computer 702, or portions thereof, may be stored in the remote memory/storage device 750. It may be appreciated that the network connections shown may be exemplary and other means of establishing a communications link between the computers may be used.

The computer 702 may be operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication may be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network may be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
   at least one memory; and
   logic, coupled to the at least one memory, operative to implement a predicted collision cross-section (CCS) process, the logic configured to:
   receive analytical information associated with a sample comprising at least one component,
   generate one or more approximate molecular models for the component via an approximate molecular modeling process, the approximate molecular model identifying a predicted three-dimensional structure of the component,
   apply a computation model configured to apply machine learning to the predicted three-dimensional structure identified by the approximate molecular model, and
   generate a predicted CCS value.

2. The apparatus of claim 1, the at least one ion mobility spectrometry instrument comprising one of an ion mobility spectrometer (IMS) or an ion mobility-mass spectrometer (IM-MS).

3. The apparatus of claim 1, the analytical information comprising at least one of drift time information, ion mobility information, or mass-to-charge (m/z) ratio information.

4. The apparatus of claim 1, the approximate molecular model comprising at least one pseudo molecular descriptor.

5. The apparatus of claim 1, the approximate molecular modeling process comprising executing a subset of cycles of a full molecular modeling process.

6. The apparatus of claim 1, the subset of cycles determined based on the structure of the component.

7. The apparatus of claim 1, the computational model comprising a machine learning process.

8. The apparatus of claim 1, the approximate molecular model comprising a plurality of possible charge states of a modeled molecule.

9. The apparatus of claim 1, the predicted CCS value within 2% or less of a corresponding experimental CCS value.

10. The apparatus of claim 1, the approximate molecular model generated in a time duration of less than 5 minutes.

11. A method for performing a predicted collision cross-section (CCS) process, comprising:
    receiving analytical information associated with a sample comprising at least one component;
    generating an approximate molecular model for the component via an approximate molecular modeling process, the approximate molecular model identifying a predicted three-dimensional structure of the component;
    applying a computation model configured to apply machine learning to the predicted three-dimensional structure identified by the approximate molecular model; and
    generating a predicted CCS value via the computational model.

12. The method of claim 11, the at least one ion mobility spectrometry instrument comprising one of an ion mobility spectrometer (IMS) or an ion mobility-mass spectrometer (IM-MS).

13. The method of claim 11, the analytical information comprising at least one of drift time information, ion mobility information, or mass-to-charge (m/z) ratio information.

14. The method of claim 11, the approximate molecular model comprising at least one pseudo 3D molecular descriptor.

15. The method of claim 11, the approximate molecular modeling process comprising executing a subset of cycles of a full molecular modeling process.

16. The method of claim 8, the subset of cycles determined based on the structure of the component.

17. The method of claim 11, the computational model comprising a machine learning process.

18. The method of claim 11, the approximate molecular model comprising a plurality of possible charge states of a modeled molecule.

19. The method of claim 11, the predicted CCS value within 2% or less of a corresponding experimental CCS value.

20. The method of claim 11, the approximate molecular model generated in a time duration of less than 5 minutes.

* * * * *